United States Patent [19]

Zadini et al.

[11] Patent Number: 5,674,239
[45] Date of Patent: Oct. 7, 1997

[54] INTRAVAGINAL BALLOON FOR BLOOD LEAKAGE PREVENTION

[76] Inventors: Filiberto P. Zadini; Giorgio C. Zadini, both of 2237 Hilltop La., Camarillo, Calif. 93012

[21] Appl. No.: 391,342

[22] Filed: Feb. 21, 1995

[51] Int. Cl.⁶ .................................................. A61M 29/00
[52] U.S. Cl. ........................... 606/193; 606/191; 606/192; 604/904
[58] Field of Search .................................. 606/191, 192, 606/193, 196, 1, 119; 604/1, 96, 99, 904

[56] References Cited

U.S. PATENT DOCUMENTS

| 1,334,237 | 3/1920 | Fleck | 604/99 |
|---|---|---|---|
| 3,154,077 | 10/1964 | Cannon | 606/192 |
| 3,701,351 | 10/1972 | Harvey | 606/192 |
| 3,841,304 | 10/1974 | Jones | 606/192 |
| 4,950,280 | 8/1990 | Brennan | 606/196 |
| 4,976,692 | 12/1990 | Atad | 604/101 |
| 5,061,187 | 10/1991 | Jerath | 434/262 |
| 5,087,244 | 2/1992 | Wolinsky et al. | 604/99 |
| 5,167,237 | 12/1992 | Rabin et al. | 128/748 |
| 5,188,630 | 2/1993 | Christoudias | 606/1 |

Primary Examiner—Michael Buiz
Assistant Examiner—Mark S. Leonardo

[57] ABSTRACT

An intravaginal inflatable member providing sealable closure of the vaginal canal for the prevention of exit of menstrual blood, or other organic fluids from the vaginal orifice. The intravaginal inflatable member can be used alone or in combination with blood absorbing devices such as intravaginal tampons for the prevention of blood leakage.

19 Claims, 9 Drawing Sheets

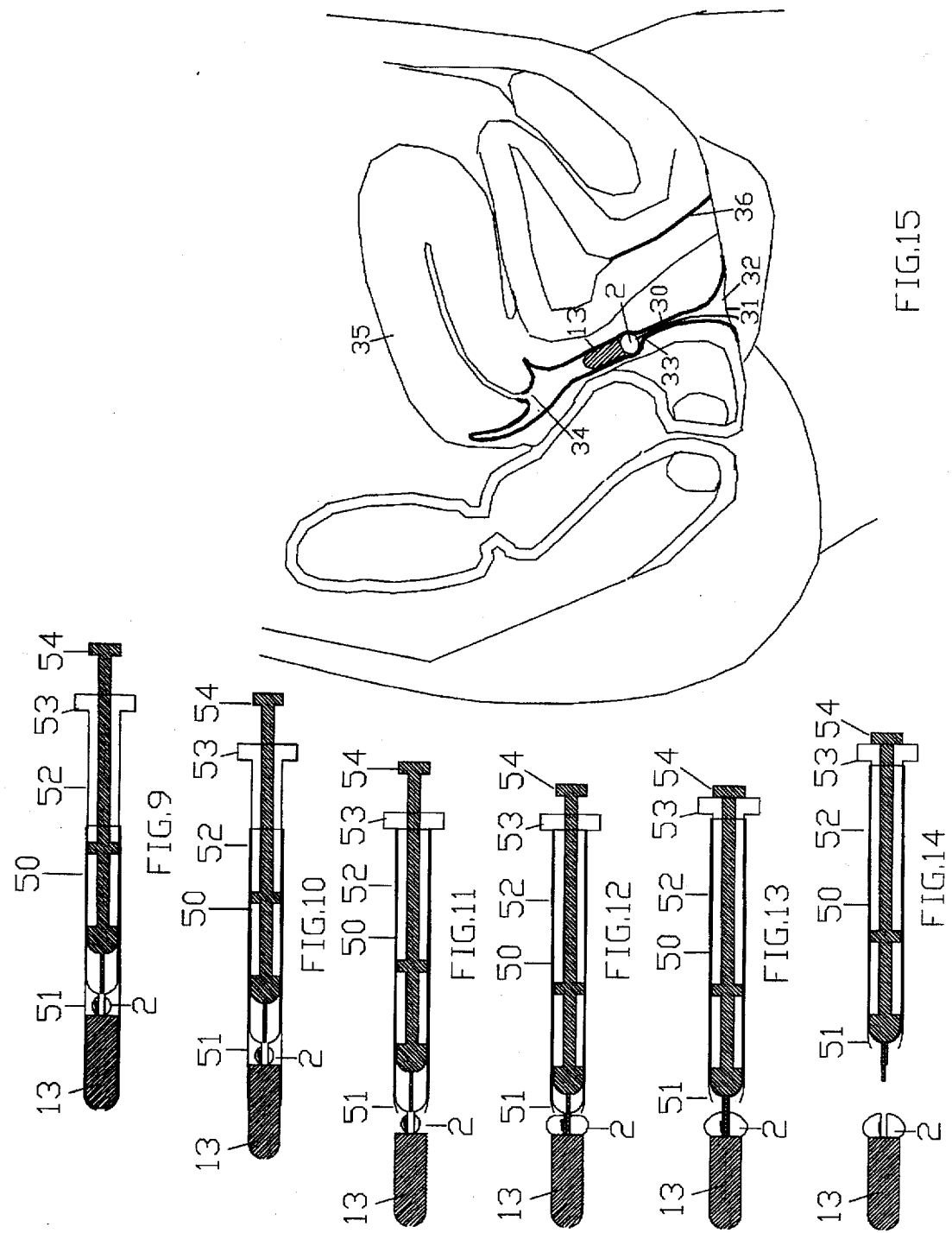

INTRAVAGINAL BALLOON FOR BLOOD LEAKAGE PREVENTION

FIELD OF THE INVENTION

This invention relates to obstetrical-gynecological devices, more specifically to intravaginal devices apt to prevent leaking or exit of blood or any other organic fluid from the vagina.

BACKGROUND—DESCRIPTION OF THE PRIOR ART

The vagina is a musculomembranous tubular organ extending from the uterine cervix to the exterior of the body. The vaginal canal is about 9 or 10 cm long. Its lumen is generally quite small, and the walls that surround it are usually in contact with each other. Various are the organic fluids which pass through the vaginal canal during the female lifetime, such as blood, vaginal secretion fluids, amniotic fluid, etc.

An important organic fluid passing through the vaginal canal and exiting through the vaginal orifice is blood, either as a result of physiological conditions such as the menstrual period or as a result of pathological conditions such as cervical or endometrial carcinoma. The various inconveniences to women resulting from the occurrence of physiological bleeding occurring during the menstrual period have prompted attempts to regulate or control the outflow of menstrual bleeding according to the women personal and social needs. For the purpose of controlling the outflow of menstrual blood, vaginal tampons were introduced a few decades ago. Vaginal tampons are common catamenial devices made of absorbing material and insertable into the vagina by the female user. Due to their absorbing material, tampons, once inserted into the vagina, begin to absorb upon contact the blood they meet, which outflows from the cervical canal into the vagina, and function as reservoirs aiming at delaying exit of the blood from the vaginal orifice conceivably until they become saturated with blood and, in so doing, they exert a regulatory effect on the outflow of menstrual bleeding to meet women's needs or preferences.

However, regardless of their absorbency capabilities, tampons, for various reasons, are known to allow leakage of menstrual blood at rather unpredictable time or shortly after insertion, falling short of providing the regulatory effect which is the very reason for their use. No known tampon is capable of preventing leakage of blood from the vaginal orifice, regardless of shape, size, intravaginal resting site, absorbency capabilities of the material or materials of which they are made of, etc. Blood may leak from the vaginal orifice because the tampon is too early saturated with blood or because the blood flow is disproportionately heavy for the absorbency capabilities of the inserted tampon or because the tampon does not provide an adequate sealing with the vaginal walls or orifice or for all the above reasons variously combined.

Despite the use of tampons, therefore, leakage of blood from the vaginal orifice is almost the rule during the days of the vaginal bleeding and its occurrence may result in a great deal of annoyance and inconvenience to the woman: leakage indeed actually defeats the main purpose for which tampons are used.

Prior art deals with the problem of leakage of the tampons, some inventions by providing additional blood reservoirs to the tampons, some others by increasing the tampons absorbing capabilities by the means of improved absorbing material, and others by using absorbing pads to apply in correspondence of the vaginal orifice to capture the blood escaped from the tampon. In all such cases, main object of the prior art is rather to minimize and possibly delay the outflow of blood, rather than reliably preventing the leakage of blood until it is the appropriate time for the woman, as determined by the woman rather than by her endometrium, to permit exit of the menstrual blood from the vaginal orifice.

No known catamenial device has been disclosed to provide means of preventing leakage of menstrual blood by entailing the use of an intravaginal balloon.

BRIEF SUMMARY OF THE INVENTION

The present invention comprises an intravaginal inflatable member capable of providing reliable vaginal closure to outflow of organic fluids such as menstrual blood from the vaginal orifice until the woman determines to be the appropriate time for allowing exit of the menstrual blood from the vaginal orifice, and also provides reliable vaginal closure to pathological bleeding. Vaginal closure is achieved by an inflatable member, impermeable to fluids, easily self-adaptable to the variability of size and shape of the vaginal lumen and to the variability of smoothness of the vaginal walls, said inflatable member expanding to exert a gentle pressure on the vaginal mucosa, such a pressure being sufficient to prevent passage of blood between the inflatable member itself and the vaginal mucosa.

The device may be used alone, as a stand-alone intravaginal device, or may be used in combination with blood absorbing means such as tampons. When combined with tampons, the device may be arranged with tampons in a number of ways, some of which will be disclosed in the detailed description of the invention.

When used in cases of pathological vaginal bleeding, the inflatable intravaginal member, comprising material substantially impermeable to fluids, expands to exert pressure on the vaginal mucosa to prevent passage of blood between the inflatable device and the vaginal mucosa, such prevention of passage of blood resulting in a blockage to intravaginal transit of blood.

OBJECT OF THE INVENTION

It is an object of the present invention to propose a device that conceivably offers a solution to the problem of untimely leakage of menstrual blood. As such, i.e. if employed as a means for prevention of leakage of menstrual blood, one embodiment of the present invention could be used, preferably, in combination with blood absorbing material, such as tampons.

However, it may also be used alone to provide means for prevention of blood leakage, or, for that same purpose, it may be used in combination with other devices or suitable components employed in association with menstrual bleeding.

It is another object of the present invention to offer a device capable of assuring prevention of blood leakage regardless of the anatomical size, shape, changing of direction and of lumen contour of the vagina, as a result of remarkable adaptability to anatomical size, shape, contour of the vagina, and adaptability to contingent changes of size, shape, lumen contour of the vagina, to maintain its outer surface in close contact with the vaginal mucosa and offer a sealing closure to blood in any condition.

It is another object of this invention to propose an inflatable device capable of reliably achieving prevention of leakage of menstrual blood while being easy to be worn, conceivably adding no discomfort to the female user, by gently applying upon the vaginal mucosa a pressure just barely sufficient to prevent passage of blood between the device and the vaginal mucosa, such a pressure being generally proportional to the pressure, notoriously negligible, exerted by menstrual blood.

It is another object of this invention to propose an inflatable device capable of reliably achieving prevention of leakage of menstrual blood, while being easy to insert and likewise easy and comfortable to extract.

It is an other object of the present invention to provide an intravaginal device capable of preventing, when indicated, leakage or outflow, in any amount, of organic fluids in general, besides blood, from the vaginal orifice.

It is an object of the present invention to provide an inflatable intravaginal device offering means of prevention of significant hemorrhage in cases for instance of pathological bleeding, by reliably preventing excessive blood loss from the vagina, by limiting the amount of blood extravasation to an amount not exceeding the maximum capacity of reservoir of a tract of the vagina proximal to the site of placement of said inflatable device, as a result of a blockage exerted by such inflatable intravaginal device on the vaginal transit of blood. A device of this kind may prevent the serious medical complications associated with massive vaginal-uterine bleeding and at times may well be a life saving device.

DRAWING FIGURES

FIG. 9 through 14 show a pneumatic pressure delivery device incorporated into a vaginal tampon applicator at different stages of operation.

FIG. 15 shows the device of FIG. 2 shown in situ, i.e. inserted and resting inside the vaginal canal and accomplishing the function of impeding exiting of blood from the vaginal orifice.

DETAILED DESCRIPTION OF THE INVENTION

Figure 1:
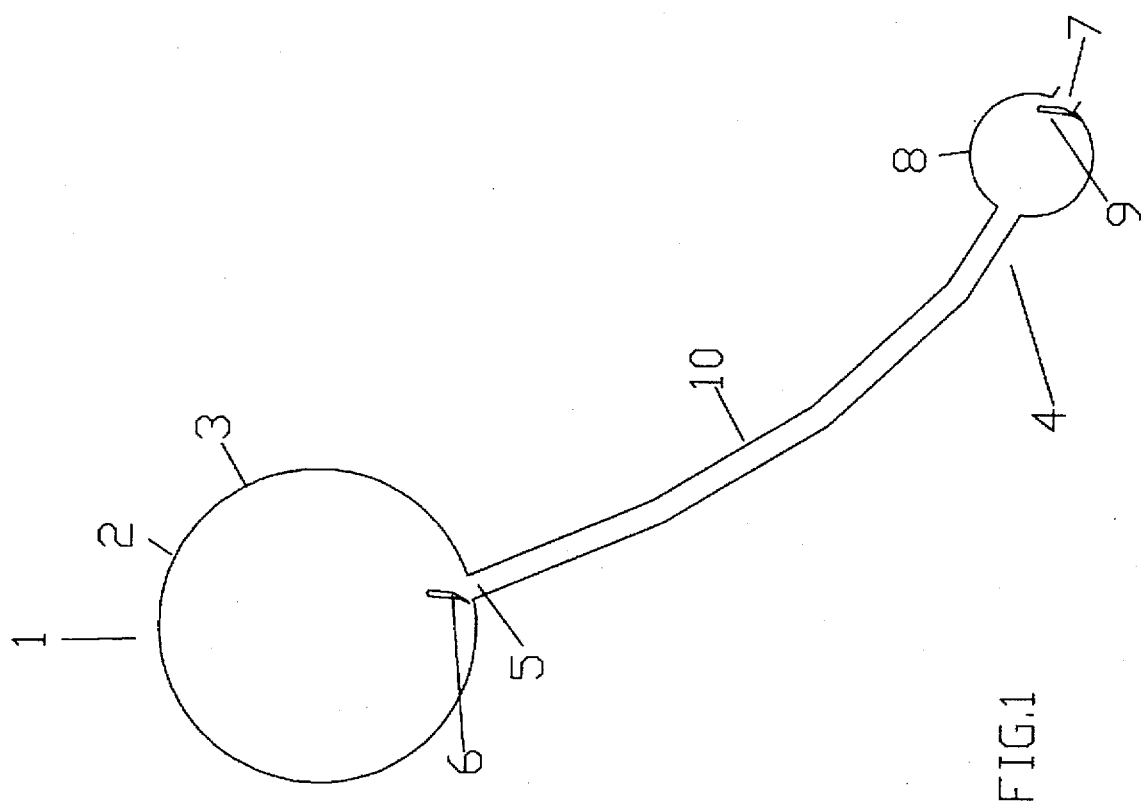
FIG. 1 is a side view of the device as it appears in operation, i.e. after inflation.

A typical embodiment of the invention is illustrated in FIG. 1. The device generally indicated at 1 is composed of an inflatable or expandable member or means or balloon 2 and pneumatic pressure delivery system or inflating means 4.

Balloon 2 has walls 3, unidirectional valve 6, which can be constructed as a pivoting flap, operating in inlet 5 of tubular member or conduit 10 of inflating means 4. Inflating means 4 is composed of pressure delivery source or pump or bladder 8 with air intake opening 7 provided with unidirectional pivoting flap valve 9, and tubular member or conduit 10 connecting pump 8 to balloon 2 via valve inlet 5 through unidirectional valve 6.

Balloon 2 can be made of material substantially impermeable to fluids.

Inflatable member 2 may be coated with a suitable means which by interfacing between the balloon and the vaginal walls provides reversible sealing with the vaginal walls as it will be disclosed in the description of the operations.

Such interfacing means could include filtering means which selectively allows passage of air or suitable gas while preventing passage of blood or organic fluids.

The inflatable member 2 can be constructed as a self-deflatable member after a predetermined time of inflation.

Such a feature can be achieved with micro porous material allowing air to escape from the inflatable member after inflation at a substantially predetermined rate of a change in permeability to air of a suitable material included in said inflatable member, said change in permeability allowing air to escape from the inflatable member at a substantially predetermined time following inflation of the inflatable member.

Figure 4:
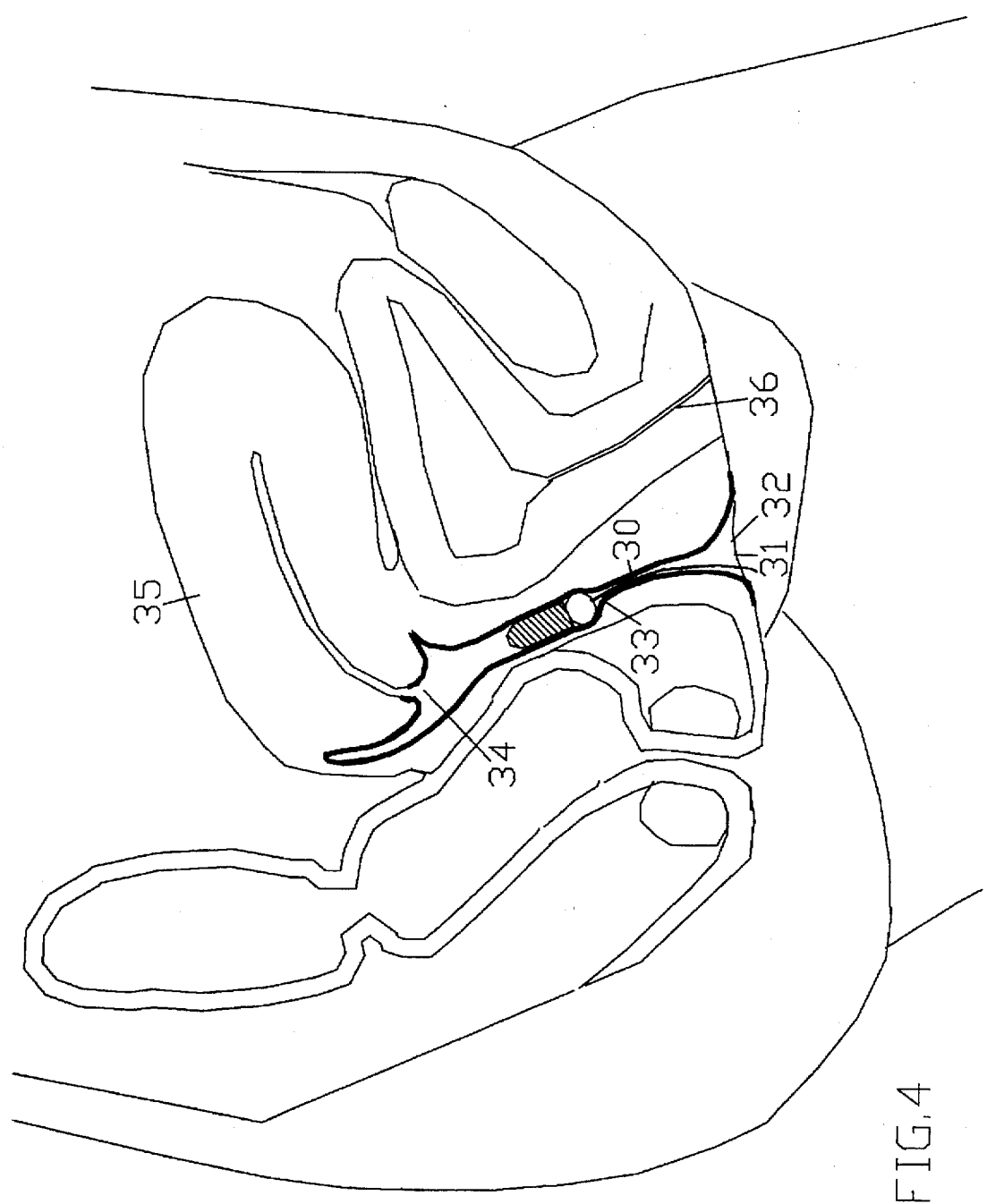
FIG. 4 is a cross sectional view of the human female pelvis.

In operation balloon 2 is inserted by the operator or user in vagina in a deflated status. As shown in FIG. 4, balloon 2, once inserted into the vaginal canal or vagina 30 beyond vaginal orifice 32, is inflated by the operator-user by means of pumping air or other suitable gas or fluid inside balloon 2 via conduit 10 by acting on pump 8. Balloon 2 will be expanded by the user-operator acting on pump 8 until wall 3 of balloon 2 become in contact, in an expanded status, with vaginal walls 33 of vagina 30.

Balloon 2, when expanded, will not permit exit of any organic fluid such as blood from vagina 30 by sealing the walls 33 of vagina 30 to walls 3 of balloon 2. Indeed expanded balloon 2 obliterates the space between balloon walls 3 of balloon 2 and, vaginal walls 33. Balloon 2 is easily extracted from the vagina orifice 32 by pulling on conduit 10 or alternatively by pulling on other means such as a string connected to balloon 2. The operator or user, by pulling on conduit 8 or on the just described string, will decrease the transverse diameter of balloon 2, facilitating its exit from vaginal orifice 31.

Figure 2:
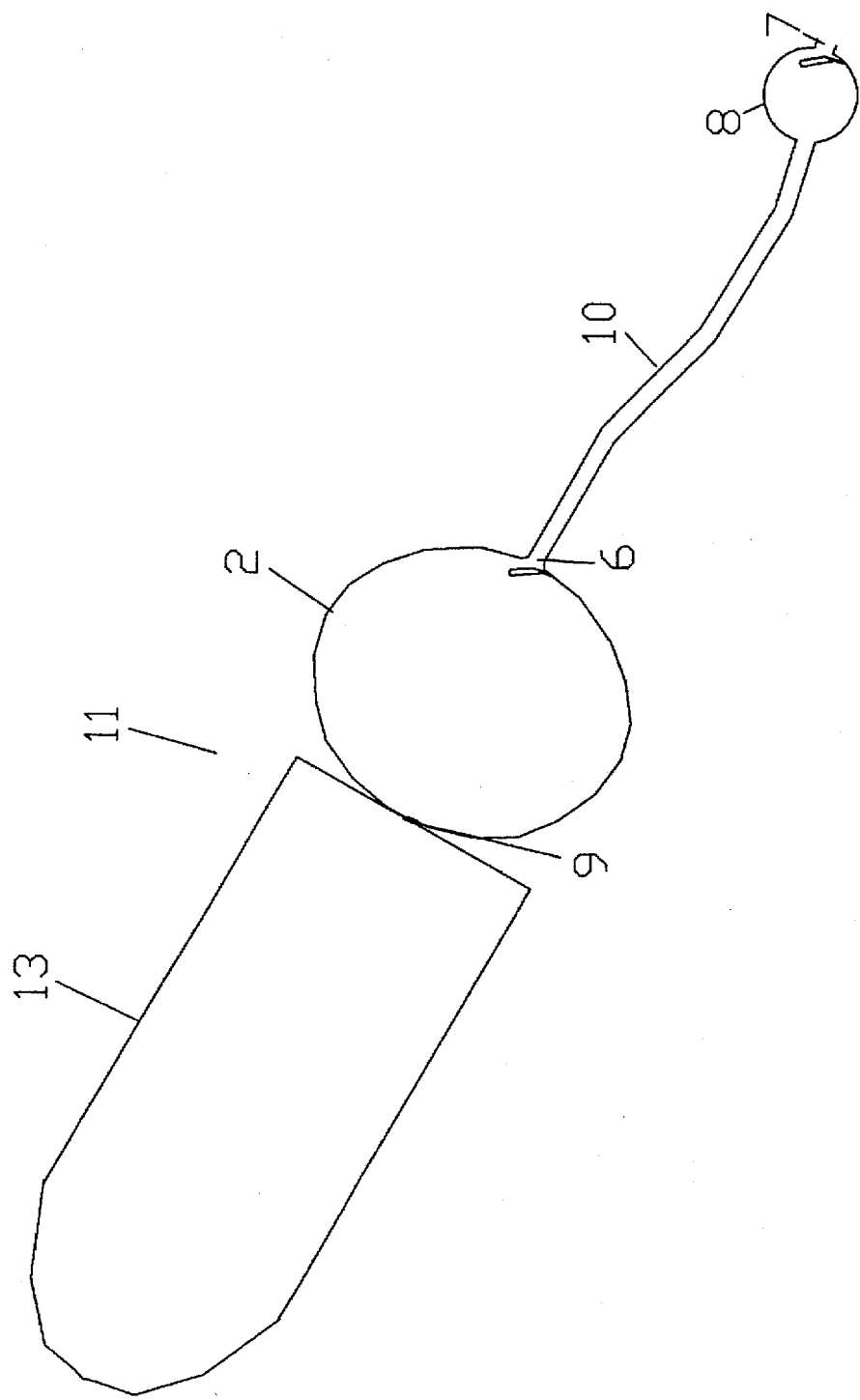
FIG. 2 is a side view of an alternative form of the device shown after inflation.

FIG. 2 shows another version of the device, generally indicated at 11. In this version balloon 2 is connected to blood absorbing means or vaginal tampon 13. The device is operated exactly as device 1. Tampon 13 will provide absorbent action for the blood. Blood which escapes tampon 13 is impeded to exit from vaginal orifice by expanded balloon 2.

Figure 3:
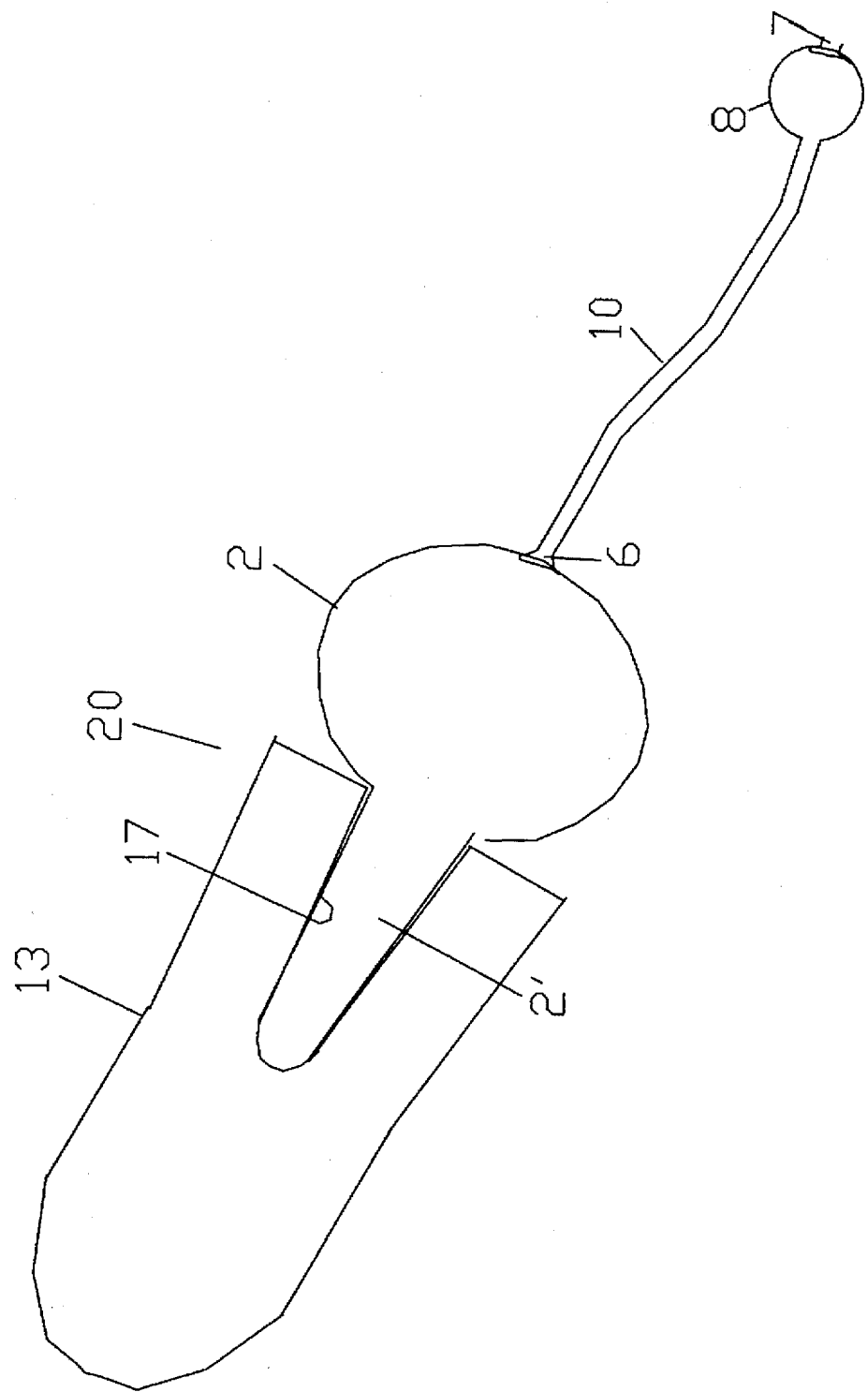
FIG. 3 is a side view of an alternative form of the device shown after inflation.

FIG. 3 shows another version of the device, generally indicated at 20. In this version balloon 2 has extension 2' engaging correspondent recess 17' of blood absorbing means or tampon 13.

In use, after insertion in vagina, balloon 2 is inflated as described for devices 1 and 11. Balloon extension 2' will also inflate as soon as tampon 13 will soften due to absorbency of blood providing little resistance to radial expansion of extension 2' of balloon 2. In this device, tampon 13, being pressed against wall 33 of vagina 30 by the expanded extension 2' of balloon 2, will contribute to the sealing by obliterating any gap between tampon 13 and vaginal walls 33. Balloon 2, as in the two other described devices, will provide sealable closure of vaginal canal 30.

Figure 5:
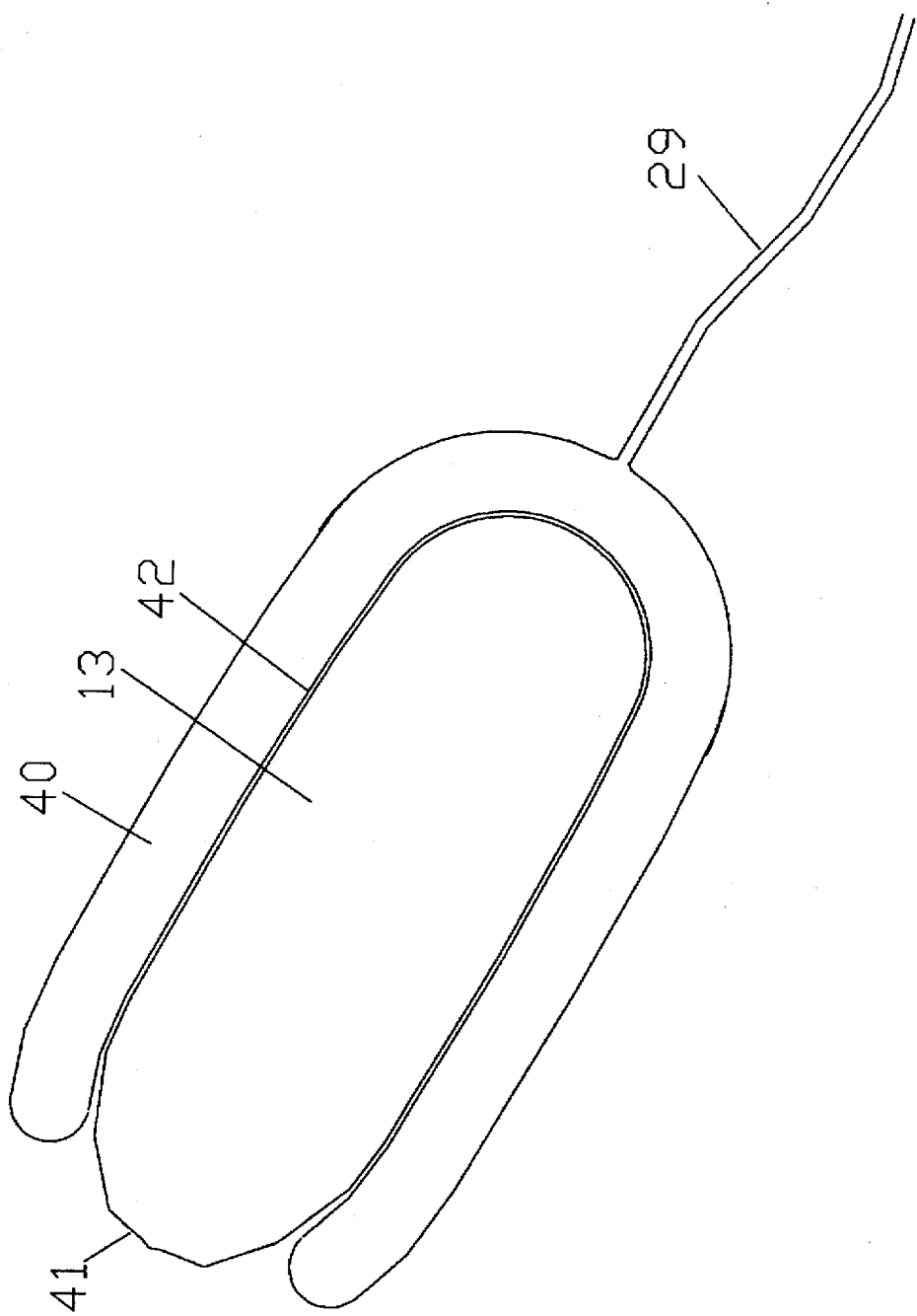
FIG. 5 is a side view of an alternative form of the device shown after inflation.

FIG. 5 shows yet an alternative form of the device, where balloon 40 is cup-shaped harboring tampon 13. In this version blood will be forced to enter distal end 41 of tampon 13 as balloon 40 encircles tampon 13 except in correspondence of distal end 41 of tampon 13, sealing side 42 of tampon 13.

Figure 6:
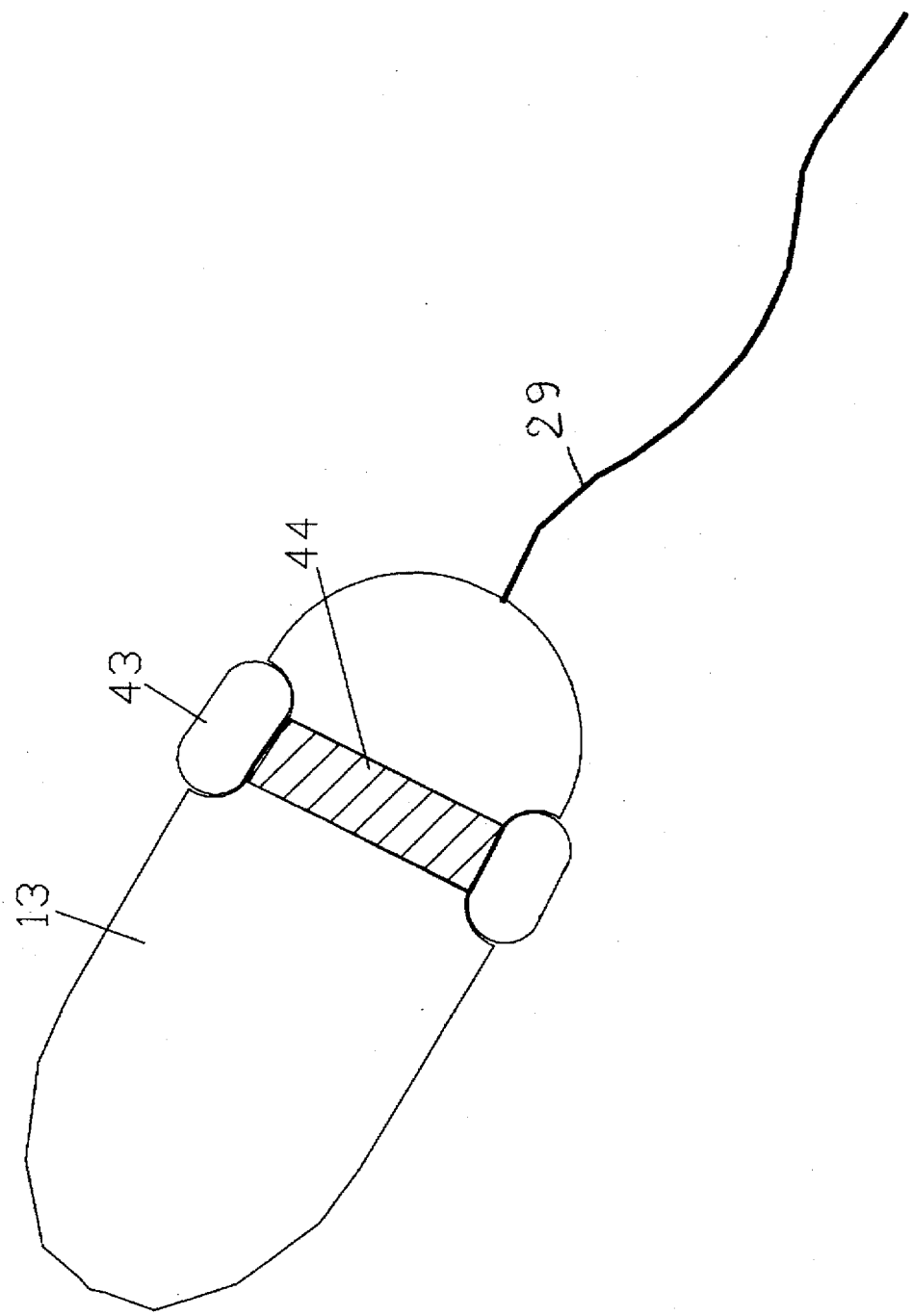
FIG. 6 is a side view of an alternative form of the device shown after inflation.

FIG. 6 shows an embodiment where the inflatable member 43 is concentric to, and sealed to, a segment 44 of any intravaginal menstrual blood absorbing means or tampon 13, where said segment 44 is adapted to be impermeable to fluids. In such an embodiment the inflatable member 43 expands to exert a pressure on the vaginal walls 33 of vagina 30 to seal to fluids the space between the inflatable member 43 and the vaginal walls 33, providing, in combination with the adapted segment 44 of a tampon 13, for a blockage to vaginal transit of menstrual blood or organic fluids.

Figure 7:
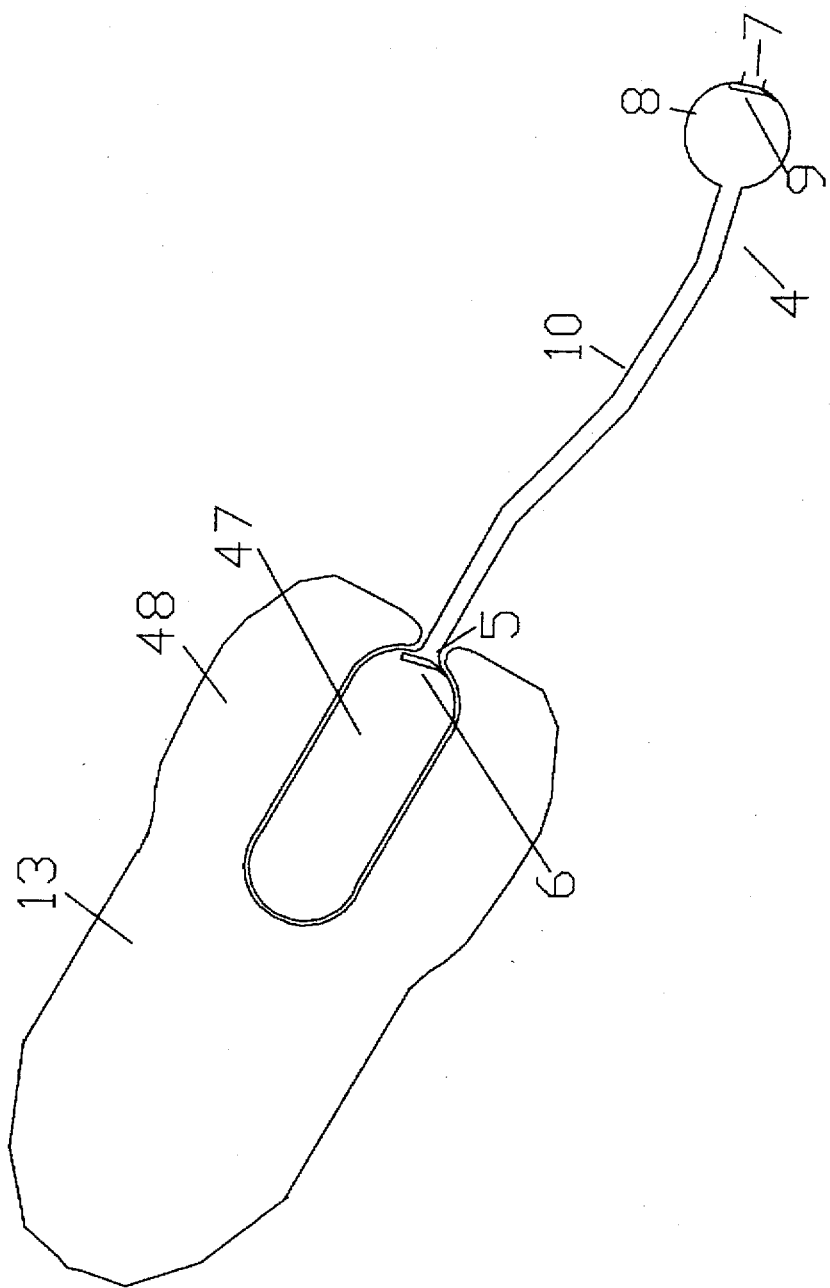
FIG. 7 is a side view of an alternative form of the device shown after inflation.

FIG. 7 shows another embodiment of the device where balloon 47 is contained in its entirety within tampon 13.

In use once balloon 47 is inflated, it will press on corresponding overlying segment 48 of tampon 13 closing the gap between vaginal walls 33 and tampon 13 by compressing segment 48 to the extent of preventing any leakage of blood.

Figure 8:
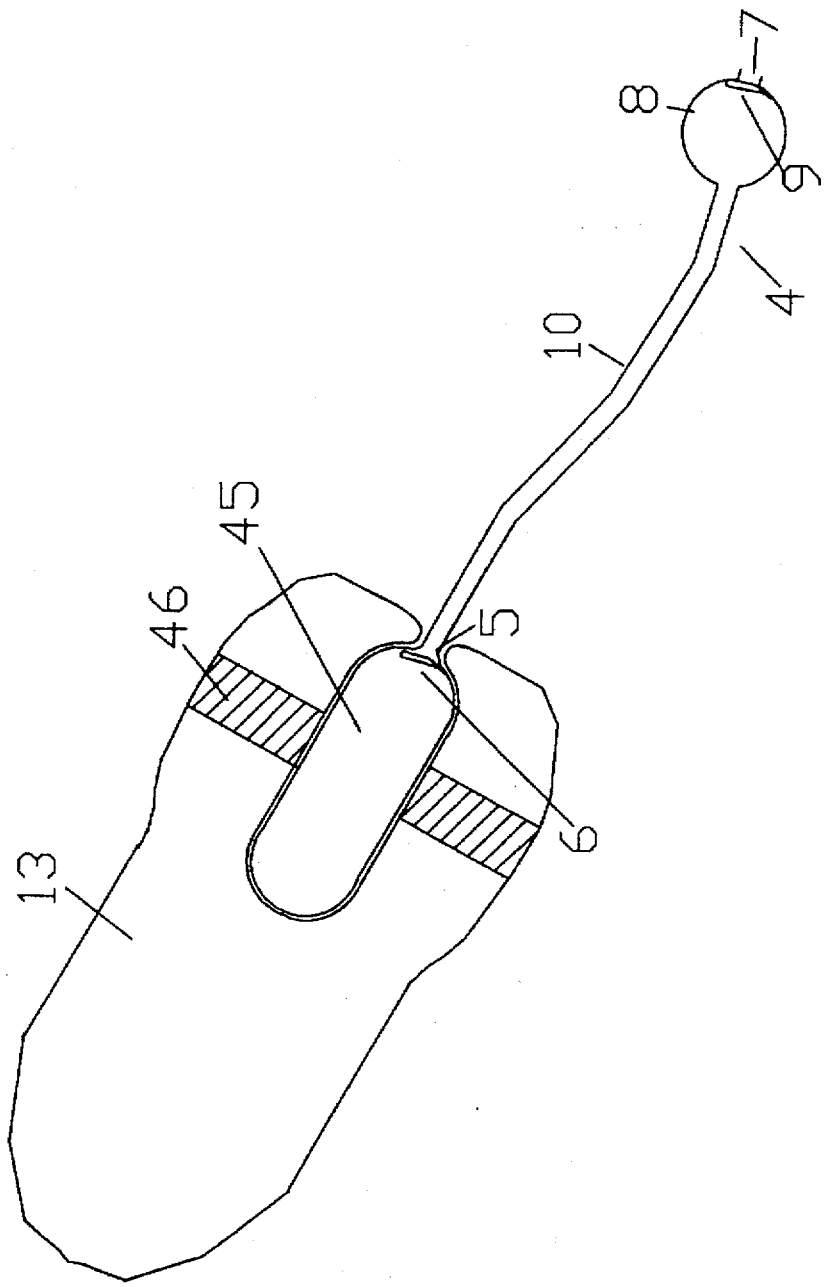
FIG. 8 is a side view of an alternative form of the device shown after inflation.

FIG. 8 shows another embodiment, where the intravaginal inflatable member 45, substantially impermeable to fluids, is contained in the interior of a segment 46 of a tampon 13. The segment 46 is adapted to be substantially impermeable to fluids. The inflatable member 45 expands to exert a pressure on the vaginal walls 33 via segment 46 of tampon 13 to seal to fluids the space between segment 46 of tampon 13 and vaginal walls 33, so as to provide, in combination with the adapted segment 46 of tampon 13, a blockage to the vaginal transit of menstrual blood.

FIG. 9 shows a pneumatic pressure delivery system or applicator-inflator 50 comprising a standard tampon applicator 51 which incorporates a syringe 52. Operator, after inserting tampon applicator 51 into vagina 30, press on syringe barrel 53, which telescopically slides within applicator barrel 51 to eject tampon 13 with its connected balloon 2 into the vaginal canal 30. FIG. 10 and 11 illustrate the insertion and delivery of tampon 13 with its connected balloon 2. As shown in FIG. 12 the user-operator, after having fully advanced syringe barrel 53 on applicator barrel 51, will act on syringe plunger 54, inflating balloon 2. As shown in FIG. 14, upon full inflation of balloon 2, further advancement of syringe plunger 54 will result in a disengagement of applicator-inflator 50 from tampon 13 and its connected balloon 2. As shown in FIG. 15, tampon 13 with balloon 2, rests firmly in vaginal canal 30, providing sealable closure of the canal, preventing any blood leakage.

We claim:

1. A catamenial device for insertion into a vaginal canal having a wall, said device comprising:
    a blood absorbing member, and
    a substantially fluid-impermeable expandable member connected to said absorbent member, said expandable member being expandable by inflation for sealingly engaging said wall of said vaginal canal upon expansion of said expandable member.

2. The catamenial device of claim 1 wherein said blood absorbing member includes an intravaginal tampon.

3. The catamenial device of claim 1 further comprising interfacing means, said interfacing means being located between said expandable member and the vaginal wall.

4. The catamenial device of claim 1, wherein said expandable member is inflatable via a pneumatic pressure delivering means where said pneumatic pressure delivering means is reversibly connectable to said expandable member.

5. The catamenial device of claim 1, wherein said expandable member is placed into said vaginal canal in a deflated status.

6. The catamenial device of claim 1, wherein said expandable member is inflatable by a syringe.

7. The catamenial device of claim 4, further comprising a tubular member in flow communication with said expandable member, said tubular member being connectable to the pneumatic pressure delivering means.

8. The catamenial device of claim 7, wherein said pneumatic pressure delivering means is a bladder, said bladder having an opening to outside environment provided with a valve means allowing entry of gas upon expansion of said bladder and preventing escape of said gas to said outside environment upon compression of said bladder, said bladder being in flow communication with said tubular member.

9. The catamenial device of claim 8 further comprising a valve means permitting passage of gas into said expandable member from said tubular member while preventing escape of said gas from said expandable member into said tubular member.

10. The catamenial device of claim 4 wherein said pneumatic pressure delivering means comprises a tampon applicator barrel carrying said blood absorbing member, said applicator barrel incorporating a syringe having a syringe barrel telescopically slideable within said applicator barrel wherein said syringe barrel is adapted to advance said blood absorbing means.

11. The expandable member of claim 10 further comprising a syringe plunger slideable within said syringe barrel where said syringe plunger is forwardly displaceable within said syringe barrel to inflate said expandable member; said pneumatic pressure delivering means being detachable from said expandable member by further advancement of said syringe plunger.

12. The device of claim 3 wherein said interfacing means includes blood absorbing material.

13. The device of claim 1 wherein said blood absorbing member has a segment substantially impermeable to fluid.

14. The catamenial device of claim 13, wherein said expandable member sealingly engages said substantially impermeable segment of said absorbing member.

15. The device of claim 1 wherein a substantial portion of a surface of said absorbing member is encircled by said expandable member.

16. The catamenial device of claim 1, wherein said expandable member is rearwardly positioned of said blood absorbing member.

17. The catamenial device of claim 1 wherein said expandable member is self deflatable after a predetermined time of use.

18. The catamenial device of claim 1 wherein said expandable member is expandable via hydraulic means.

19. The catamenial device of claim 1 wherein said interface means include a filtering means which selectively allows passage of air while preventing passage of blood or organic fluids.

* * * * *